United States Patent [19]

Hill

[11] 4,012,839

[45] Mar. 22, 1977

[54] METHOD AND COMPOSITION FOR TREATING TEETH

[75] Inventor: William H. Hill, St. Paul, Minn.

[73] Assignee: Peter Strong & Company, Inc., Portchester, N.Y.

[22] Filed: Nov. 26, 1973

[21] Appl. No.: 418,997

[52] U.S. Cl. .................................. 32/15; 424/129; 424/210

[51] Int. Cl.² ........................................ A61K 5/02

[58] Field of Search ............ 424/290, 132, 129, 49, 424/54; 32/15

[56] References Cited

UNITED STATES PATENTS

| 1,740,543 | 12/1929 | Gerngross | 424/129 |
| 2,981,640 | 4/1961 | Hill | 117/138.5 |
| 3,421,222 | 1/1969 | Newman | 32/15 |

OTHER PUBLICATIONS

Dental Abstracts, "Silver Nitrate Treatment of Proximal Caries in Primary Molars", p. 272, May 1957.

*Primary Examiner*—Robert Peshock
*Attorney, Agent, or Firm*—Thomas M. Meshbesher

[57] ABSTRACT

In the well-known technique of disinfecting caries-infected or potentially caries-infected dental tissue with silver nitrate, silver thiocyanate or its complexes have been substituted for silver nitrate with excellent disinfecting results and lowered side effects, e.g., with lowered toxicity toward dental tissues and mouth membranes and less blackening of exposed portions of the teeth.

16 Claims, No Drawings

METHOD AND COMPOSITION FOR TREATING TEETH

FIELD OF THE INVENTION

This invention relates to a method for treating mammalian dental tissue with a bactericidal amount of a silver salt. An aspect of this invention relates to the disinfecting of carious or portentially carious tissue with a light stable silver salt (including a complex salt such as a coordination complex or a double or triple salt), which can be in the form of a solution, a dry powder, a suspension, or a dispersion (e.g. a water-based paste). A further aspect of this invention relates to an improvement upon the known technique for preparing teeth for therapeutic purposes such as filling with a coventional amalagm or other filling material or the application of caps. Still another aspect of this invention relates to an improved substitute for silver nitrate solution or Howe's Solution in the treatment of dental caries (tooth decay).

DESCRIPTION OF THE PRIOR ART

Dental caries (tooth decay) is a complex disease which is believed to involve polysaccharide-producing flora present in the mouths of mammals on a "soft" food diet. (Dental caries can be produced in monkeys, rats, hamsters, and the like, as well as humans, if these animals are placed on a diet approximating the human diet.) It is known that bactericidal or bacteriostatic chemicals of low toxicity can be used to some extent in inhibiting tooth decay. It is also well known that silver salts have bactericidal activity.

The preparation of teeth for therapeutic purposes, such as filling with the conventional dentally acceptable metal amalgam or other filling material or the application of caps, has always been a vexing problem. Even with the most careful removal of carious tissue, the continued action of residual bacteria can lead to renewed destruction of dental tissue (e.g. enamel, dentin, pulp, etc.), and a classical technique for dealing with this continued decay action is to treat the affected area with silver nitrate in aqueous solution or the silver nitrate/ammonia complex solution known as Howe's Solution. For example, one application of this technique is to prepare the affected area by mechanical removal of as much carious tissue as possible and then rub the mechanically prepared cavity with a cotton pellet impregnated with the silver nitrate solution or Howe's Solution. This technique has been shown to be effective in inhibiting or preventing renewed caries in the treated teeth. However, undesirable side effects, such as blackening of the teeth and, above all, possible injury to and death of the pulp of the teeth eventually led to virtual abandonment of this otherwise promising disinfecting technique. Pulpal injury and even death has been reported by papers by prominent U.S. dentists through photo micrographs of thin sections of treated teeth. Moreover, the use of silver nitrate in aqueous solution or as Howe's Solution was burdened by the disagreeable coloration and even blackening of the dentist's hands, his and his patient's garments, towels, table tops, etc.

Besides silver nitrate, other silver salts are known to be bactericidal and useful even in the presence of animal tissue such as mucous membranes. For example, in U.S. Pat. No. 1,740,543 (Gerngross et al), issued Dec. 24, 1929, the use of a combination of silver cyanide and potassium or barium thiocyanate as a relatively non-irritating disinfectant is disclosed.

Silver thiocyanate (AgSCN) is known to be both bactericidal and relatively light stable; see U.S. Pat. No. 2,981,640 (Hill), issued Apr. 25, 1961. The Hill patent teaches the use of AgSCN or mixtures thereof with other thiocyanates to treat or sterilize cloth articles through precipitation of the silver thiocyanate onto the article from a solution or by applying a suspension of the silver thiocyanate to the article. The Hill patent also teaches that excess thiocyanate ion, $SCN^-$, improves both the light stablility and the solubility of the silver thiocyanate salt. The patent further points out that ammonia can also be used to improve the solubility of the silver thiocyanate. Anti-bacterial activity reported in the Hill patent and elsewhere indicates that silver thiocyanate has reasonably broad spectrum bactericidal effects.

Theoretical studies indicate that the solubilization of the silver thiocyanate in aqueous media such as aqueous solutions of ammonia or water-soluble thiocyanates apparently involves the formation of complex salts, e.g. double or triple salts, coordination complexes, and the like. Several silver thiocyanate complexes have been disclosed in the literature, including double or triple salts of silver thiocyanate and alkali metal or ammonium thiocyanates. Another known complex is reported to be a triple salt of silver thiocyanate, ammonium thiocyanate, and ammonium thiosulfate. According to the findings in the literature, a variety of mole ratios are possible in these complex salts, e.g., a pentavalent argentate containing six thiocyanates has been reported.

SUMMARY OF THE INVENTION

It has now been discovered that the classical technique of disinfecting carious dental tissue with a silver salt can be markedly improved if the silver salt is silver thiocyanate or a complex salt thereof. Prior to this invention, there was apparently no available findings with regard to the effect of silver thiocyanate or its complexes on cariogenic bacteria or dental or other oral tissues. It has now been found that silver thiocyanate and its complexes are surprisingly low in toxicity with respect to dental tissues, mucous membranes, etc. In the bactericidal amounts commonly used in the art of dentistry (e.g. in preparing teeth for fillings or caps), silver thiocyanate compositions of the method of this invention have been found to have a toxicity approximately equal to that of conventional denture adhesives, on a commonly accepted scale of toxicity. The effect of these compositions on mouth membranes has now been found to be virtually negligible — very much less than that of a silver nitrate solution of equal concentration. Even more striking, research with monkeys (which are becoming increasingly accepted as a model for humans in dental caries research) demonstrates that treatment of tooth cavities, excavated almost to the pulp area, with solutions prepared according to this invention (e.g. silver thiocyanate/ammonium thiocyanate aqueous solutions) did not injure the pulp. In comparative tests with Howe's Solution, severe injury to the pulp was noted.

In addition to the surprisingly low toxicity of the solutions used in this invention, several additional advantages have become readily apparent. The inhibition or prevention of cariogenic activity and the spectrum of anti-bacterial activity appears to be at least equal to aqueous silver nitrate or Howe's Solution. Unlike the classical silver nitrate or Howe's Solution technique, blackening of the teeth, hands, garments, etc. is not a problem. The non-staining nature of silver thiocyanate and its complexes permits use of these compounds on frontal teeth as well as buccal teeth, while silver nitrate or Howe's Solution could only be used on the latter, where subsequent discoloration had no undesirable cosmetic effect.

It might be expected that the low solubility of slver thiocyanate might result in poor shelf life for its solutions in water or other polar media, even if the polar liquid medium contains solubilizing materials such as the alkali metal, alkaline earth metal, or ammonium thiocyanates. In some prior art applications of the silver thiocyanate technology, solubility is not an important factor, since the objective is to precititate the silver salt onto fabric or the like. It has now been found that silver thiocyanate complex salt solutions prepared according to the teachings of this invention have adequate shelf stability for use in dentistry.

DETAILED DESCRIPTION OF THE INVENTION

As pointed out previously, dental caries is primarily a problem peculiar to humans, although many satisfactory mammalian models for research are known, including rats, hamsters, and monkeys. Research has demonstrated that oral acceptability in mammals (including humans) can have wider tolerance limits (in terms of lethal dosages) than pharmaceutical acceptability for many types of parenteral administration. Thus, the classical silver nitrate technique for disinfecting teeth, though somewhat harmful to dental tissues, was safe in terms of overall human toxicity and effective in terms of caries inhibition.

From the experimental data obtained in connection with this invention (including human and animal trials and microbiological studies), it is now apparent that the silver thiocyanate compositions used in the invention are safer than, yet at least as effective in inhibiting caries as silver nitrate solutions per se or Howe's Solution. Not only is overall human toxicity negligible when these compositions are used orally in bactericidal amounts, the local effects on dental tissues and mucuous membranes of the mouth are surprisingly less severe as compared to the classical silver nitrate technique.

Accordingly, the silver salt compositions of this invention can simply be substituted for silver nitrate or Howe's Solution in the classical technique with improved results. No modifications in the technique for preparing the teeth are necessary. For example, in filling viable teeth, the carious tissue (enamel, dentin, pulp, etc.) is removed to the greatest extent possible with mechanical means such as the conventional drilling technique. As is known in the art, even the most careful mechanical removal can leave behind some cariogenic sites adjacent to the cavity or the affected area. These cariogenic sites can be treated according to this invention in the same manner typically used for application of silver nitrate or Howe's Solution. That is, a more or less concentrated aqueous solution of a silver salt compositon of a method of this invention can be applied at least to the inside of the fillable cavity using an absorbent applicator, e.g., a cotton pellet. The absorbent applicator is rubbed into the cavity by hand pressure, so as to force the disinfectant material into the dental tubules as much as possible. Movement of the body fluids will thereafter carry silver thiocyanate or its complexes further into the tooth structure where it will do its job as an excellent bactericide of broad spectrum effectiveness.

However, the practice of this invention is not limited to the use of aqueous solutions. Solutions in sufficiently pure, orally acceptable polar solvents such as dimethyl sulfoxide can be used. Of course, all polar solvents are not equally acceptable and do not work with equal effectiveness, and distilled and/or deionized water is the preferred orally acceptable extending medium. The silver thiocyanate or complex salt of silver thiocyanate can be applied to the carious tissue in the usual milligram quantities (e.g. 1–100 mg per application, per tooth) as a dry powder made from the crystallized or recrystallized salt, alone or with a solid extending medium (e.g. a colloidal silica such as "Cab-O-Sil", trademark of Cabot Corp.). Aqueous or other liquid suspensions or dispersions can be used in accordance with techniques known in the arts of medicine and dentistry, more or less in the same manner that concentrated solutions are used. Another orally accepted form of the silver thiocyanate or its complexes is a thick paste which can, for example, be made up in a manner analogous to the production of dentifrice paste. All paste-like compositions do not work with equal effectiveness, and aqueous pastes are preferred.

As is known in the art of disinfecting teeth with silver nitrate, a reducing agent can be applied to the treated area to precipitate metallic silver in the tooth cavity. Formaldehyde and eugenol have been used for this reduction step. While these agents are useful also in connection with silver thiocyanate and its complexes, they are not preferred bacause of their irritant and even denaturant effects. The reducing agents preferred for use in this invention are the water soluble hydrosulfites, e.g. sodium hyrosulfite, which provide rapid reduction of the silver salts to metallic (black) silver and yet are relatively non-toxic and non-irritating in the form of the dilute aqueous solution which would be used for such a purpose, e.g. a solution at a concentration within the range of about 0.1–5% by weight.

Once the carious tissue has been mechanically removed and the ramaining cariogenic or potentially cariogenic sites disinfected according to the teachings of this invention, the teeth are prepared for the ultimate therapeutic purpose, such as filling with one of the conventional dental filling noble metal/mercury amalgams. As will be readily apparent to those skilled in the art of dentistry, the advantages and technique of this invention are also applicable to the preparation of teeth for other therapeutic purposes such as capping.

Although the application of silver thiocyanate chemistry to the problem of disinfecting teeth can be accomplished through a relatively straightforward substitution of an aqueous solution of a silver thiocyanate complex for the classical aqueous silver nitrate or Howe's Solution, a detailed consideration of the chemistry of silver thiocyanate has been found to provide several different useful embodiments for the practice of this invention.

CHEMISTRY OF AgSCN

The thiocyanate ion ($SCN^-$) is known in the art as a "pseudohalogen" and has been found to possess some unique properties. For example, aqueous calcium or ammonium thiocyanate is an excellent hydrotropic solvent capable of dissolving many organic compounds and materials and will even swell cellulose. Silver thiocyanate is affected very little, if at all, by light — a rather unique property as compared to other silver salts such as silver nitrate and the silver halides. The complex salts of silver thiocyanate (e.g. double and triple salts of AgSCN with other thiocyanates such as those of ammonia, alkali metals, and alkaline earth metals) are, if anything, even more resistant to light-induced degradation or reduction.

While silver thiocyanate per se is extremely water insoluble, only 0.00021 grams disolving in 100 ml of water at 25° C., solubility is increased considerably when it is complexed with more water soluble thiocyanates, e.g. those of the alkali and alkaline earth metals or ammonium. As pointed out previously, several such complexes are reported in the literature and are generally presumed to be multiple salts, e.g. double or triple salts, although coordination complexing may also be a factor in their molecular structure.

According to the scientific literature, these complex salts can be prepared in solutions in polar media (e.g. water) and can be recovered as crystallized or recrystallized solids, by evaporating part or all of the solvent medium, by appropriate reduction in temperature of the solutions, and by other means well known to those skilled in the art.

Stable solutions of silver thiocyanate complex salts can contain as much as a 30% (either weight/weight or weight/volume) equivalent of silver nitrate and even more. In these solutions, the silver apparently has become part of the anion. Based on findings reported in the literature, the general formula for such complexes can be characterized as follows:

$$[Ag(SCN)_x]M_y$$

Wherein M represents an orally acceptable, water soluble metallic or ammonium cation, $x$ represents a number equal to at least about 2 (e.g. 2 – 6 and possibly more), and $y$ represents a number equal to at least 1 (e.g. 1 – 5 and possibly more).

In typical complex salts of this nature, M is sodium, potassium, lithium, or $NH_4$, $y$ is 3, and $x$ is 4. In other typical complexes, M is calcium, strontium, or some other orally acceptable alkaline earth cation. M can also be zinc or a trivalent metal such as aluminum. When M is an ammonium radical, several different values for $x$ and $y$ are known, e.g. $x = 3$, $y = 2$; $x = 2$, $y = 1$; $x = 6$, $y = 5$; etc. When M is potassium or sodium, $x$ and $y$ can also vary, e.g. $x = 3$, $y = 2$; $x = 2$, $y = 1$; etc. In some of the chemical literature, the formula for these complex salts is written so as to indicate a double salt of AgSCN and $M(SCN)_m$, where m is the valence of M.

Closely related compounds also useful in this invention are those containing the thiosulfate radical in addition to the thiocyanate radical, e.g. the compound $AgSCN.NH_4SCN.4(NH_4)_2S_2O_3$. This compound, according to the findings in the literature, appears to have the same or similar structure as has been indicated previously for the complexes not containing the thiosulfate radical. However, the silver thiocyanate - thiosulfate complexes are not quite as stable as those containing the thiocyanate radical but not the thiosulfate radical, and for this reason the thiosulfate-containing complexes are not generally preferred for use in this invention.

It should be noted that the aqueous complexed silver thiocyanate solutions, extremely stable as they are in themselves, will decompose on addition of water to yield silver thiocyanate and the associated water soluble thiocyanate (e.g., ammonium thiocyanate, an alkali metal thiocyanate, an alkaline earth metal thiocyanate, etc.). The more water is added, the faster and more complete is the resultant disassociation of the component thiocyanates For this reason it is generally preferable to apply to the teeth the solutions of silver thiocyanate complexes described previously, because, on introduction to the dental cavity, such solutions penetrate into the dental tubules for a considerable distance before being dissociated or disassociated by the body fluids. When this occurs, solid silver thiocyanate is deposited in the tubules and can continue to do its bactericidal job.

In short, the preferred orally acceptable form comprises a relatively concentrated aqueous solution or dispersion (e.g., above about 5% on a wt./wt. basis) of a water soluble and/or stably dispersible salt made up of AgSCN complexed with at least one water soluble thiocyanate (e.g., an ammonium or alkali metal or alkaline earth thiocyanate). This form facilitates penetraton of dentin and dental tubules by means of, for example, the solubilizing effect of the water soluble thiocyanate or the hydrotropic solvent effects of solvents such as aqueous ammonium thiocyanate.

The preparation of silver thiocyanate itself is well known in the art and is described in inter alia, the aforementioned U.S. Pat. No. 2,981,640 to Hill. As pointed out in this patent, silver thiocyanate can be precipitated by addition of silver nitrate solution to aqueous ammonium thiocyanate until the white precipitate bagins to form. The precipitated silver thiocyanate can be redissolved with additional ammonium thiocyanate to provide any of the desired silver thiocyanate-ammonium thiocyanate complexes. The procedure is analogous when the water soluble thiocyanate is NaSCN, KSCN, $Ca(SCN)_2$, or the like. Solutions of greater or lesser silver concentration can be prepared as desired and needed by manipulating the amount of ammonium thiocyanate and/or water added to the complex salt solution. As the amount of solvent water is increased, more ammonium thiocyanate is needed to produce a clear solution; and conversely, less thiocyanate can be employed at greater concentrations of solids. Ammonia apparently solubilizes AgSCN by complexing with silver cations and/or serving as a base which forms cations for the $Ag(SCN)_x$ anions of a complex salt. Amines such as triethanolamine and others appear to behave in a manner analogous to ammonia.

In this silver nitrate/soluble thiocyanate method of synthesis, nitrate salts are produced as a byproduct. Another characteristic of this method is that two or more species of the complex may be produced, resulting in molar ratios of AgSCN-to-MSCN which are not integers. However, fractional crystalization can substantially remove nitrates and isolate specific complexes. Substantially nitrate-free complex salt and complex salt solutions are preferred.

Complexes of silver thiocyanate with relatively water soluble thiocyanates can also be made in the form of solutions or solids, free of contaminating products derived from metathetic reactions, by the following method.

Free thiocyanic acid, HSCN, is vacuum distilled at low temperatures, generally from about 20° – 50° C., from a reaction flask containing easily available thiocyanates (e.g., the alkali metal thiocyanates) and a strong mineral acid such as sulfuric acid. The vapors consisting of water vapor and HSCN are condensed in a cooled receiving flask containing water and a silver compound, e.g., silver oxide or silver carbonate. Silver thiocyanate is formed from the reaction of this silver compound and HSCN. If a sufficient excess of HSCN is distilled over, then the excess can be neutralized with a base or basic salt, resulting in direct formation of the desired complex or double salts, examples of such bases or basic salts being carbonates, oxides or hydroxides of alkali metal or alkaline earth metals (including Ca, Mg, and Sr), zinc, ammonium, amines; etc. The amount of base or basic salt used for neutralization can be selected so as to provide the desired molar ratio between silver thiocyanate and the water soluble thiocyanate. Another approach is to include sodium, potassium, or ammonium thiocyanate or the like, the silver compound, and some water in the receiving flask. The proper stoichiometric amount of HSCN vapor distilled into the receiving flask will then provide the desired complex salt in substantially preferred form, which can be crystallized or re-crystallized for purposes of isolation and additional purification. Besides silver carbonate, silver salts of other volatile acids (e.g., acetic acid) can be used in the receiving flask.

When silver thiocyanate is made by reaction between a silver salt solution and a water soluble thiocyanate, a high level of purification can also be obtained by great dilution with water, filtering, and washing the precipitate. A substantially pure silver thiocyanate complex can then be formed by adding sufficient water soluble thiocyanate to a clean aqueous slurry of the silver thiocyanate product until a clear solution is formed.

TEST RESULTS FROM DENTAL RESEARCH

As pointed out previously, it is preferred for purposes of this invention to use clear solutions of silver thiocyanate complexes, e.g., the complexes of silver thiocyanate and ammoinium-, alkali-, or alkaline earth metal (e.g. calcium) thiocyanates. Studies carried out in connection with this invention show that these solutions of the complex salts are reasonably stable in the dental tubules and are not dissociated into the essentially insoluble silver thiocyanate and the relatively soluble thiocyanate salts until the solution comes into contact with body fluids circulated to the dental tubules.

The toxicity of silver thiocyanate and particularly the silver thiocyanate complexes is generally of a low order. In fact, thiocyanate occurs in human and animal bodies as a product of detoxification, for instance, of small amounts of cyanides as they occur in some foods. Such thiocyanates have been found in the saliva of man and other mammals. Relatively large amounts of thiocyanates such as sodium or potassium thiocyanate, have been used medically for the reduction of high blood pressure. The use in medicine of silver cyanide in combination with potassium thiocyanate and other thiocyanates, though in very low silver and extremely high thiocyanate concentrations has already been noted in the discussion of U.S. Pat. No. 1,740,543. In the context of this invention, there is no advantage and may be some disadvantages in using cyanide salts in combination with AgSCN or its complexes; hence, the compositions of this invention are ordinarily essentially cyanide-free.

In actual tests, it has been found that the toxicity of preferred complex silver thiocyanate solutions of this invention is rated to be about equivalent to commercially available denture adhesives, on a commonly accepted scale of toxicities. Further tests demonstrate that the effects of these complex solutions on membranes of the mouth are less than that of a silver nitrate solution of equal concentration and are apparently negligible. As pointed out previously, work in monkeys (an increasingly accepted animal model for dental caries research) demonstrates that the dental pulp of primates is not injured by these complex solutions.

A summary of the test results obtained from a study on the excavated teeth of 3 monkeys is described subsequently in Example 3. Lethal dosage data (based on rodents) for an embodiment of this invention is reported in Example 2. Human trials have been conducted on normal and carious teeth which are to be extracted. The teeth were given typical cavity preparations, treated with the silver complex salts solution, and restored with a temporary, inert cement filling material prior to extraction. The extracted teeth were investigated for response to silver complex treatments. A significantly less severe response (as compared to Howe's Solution) was noted in the case of these extracted teeth.

For use in human dentistry in orally acceptable solution form, the preferred silver thiocyanate complex salt compositions of this invention contain 5–50%, on a weight per volume-of-solution basis, of silver salt (expressed as silver nitrate equivalent), 2–6 moles of alkali metal (e.g. Na, K), ammonium, or alkaline earth metal (e.g. Ca) per gram-atom of silver, plus sufficient deionized and/or distilled water to dissolve the silver thiocyanate complex. The solution is preferably substantially nitrate-free.

As is known in the art, orally acceptable compositions can be prepared from chemicals of sufficient purity, and water used for solutions can be de-ionized and/or distilled.

The principles and practices of this invention are illustrated in the following Examples.

EXAMPLE 1

Preparation of Complex Salts

Solutions were prepared from 600 grams (g) of chemically pure (C.P.) silver nitrate and 500 milliliters (ml) of distilled water, and from 900 g. of C.P. ammonium thiocyanate and 500 ml of distilled water, using glass vessels rather than metal containers. The solutions became cold during dissolution of the solids salts, and stirring with glass stirrers and application of mild heat was used to hasten the formation of the solutions. Once the solutions were formed, they were allowed to cool down to room temperature spontaneously.

After having reached room temperature, the two solutions were mixed by adding the silver nitrate solution in small increments to the ammonium thiocyanate solution, employing good stirring with glass paddled stirrers at a speed assuring good mixing without splashing of the mixture. A precipitate of silver thiocyanate formed as the silver nitrate solution entered the ammonium thiocyanate solution, but the precipitate subsequently dissolved, due to the complexing action in the solution. Initially, the solution was slightly pink, but this color disappeared when all the silver nitrate had been added. The final solution was clear and colorless.

During the mixing of the two reactant solutions, heat was generated due to the formation of the complex, and the temperature of the resulting solution rose to a temperature within the range of 50° – 60° C. This exotherm was absorbed by cooling the reaction mixture. Several batches were made by the foregoing procedure; a typical batch had a volume of 1,820 ml. Silver analysis indicated a silver content of 15.995%. This is in good agreement with the theoretical amount (15.24%), particularly in view of probable water losses in processing and unavoidable analytical error. The theoretical silver nitrate equivalent of the solution is 24% on a weight for weight basis and about 33% on a weight for volume basis.

In an effort to ascertain the type of complexes made by this method, preparation were made in accordance with this Example but using stoichiometrically equivalent proportions of sodium thiocyanate and potassium thiocyanate instead of the ammonium thiocyanate. The $NH_4$-Ag, Na-Ag, and K-Ag complexes were allowed to evaporate spontaneously in open vessels at room temperature until substantial amounts of crystals were formed in the solution. These were filtered off, the filter cakes dried as much as possible on and between filter paper (no blackening of the filter paper was observed), and finally dried over activated alumina in desiccators. In the case of the $NH_4$-Ag complex, a second crop of crystals was obtained after further evaporation of the filtrate from the first crop and was treated in the same manner as the other crystal crops. Analyses were performed on these crystal crops using one gram of each of the four materials. By dissolving the gram of material in one liter of deionized water, the resulting low level of concentration dissociates the complex, and solid silver thiocyanate precipitates. The solid silver thiocyanate was filtered off, dried thoroughly at room temperature, and weighed, yielding the percentage of silver thiocyanate contained in each of the four crystal crops. The filtrates remaining from these gram sample solutions were analyzed by suitable sodium, potassium, ammonium, thiocyanate, and nitrate determinations; sodium and potassium were determined by atomic absorption, thiocyanate anion in solution by silver nitrate titration, ammonia by Kjeldal distillation, and nitrate by the phenoldisulfonic acid method. The following results were obtained:

there may be two or more species of the complex incolved, with the 1:1 molar ratio predominant and smaller amounts of complexes of, apparently, 1:2, 1:3, and even higher ratios admixed therewith. The first crop of the ammonium-silver complex is a fairly high grade of ammonium nitrate with a small amount of ammonium-silver thiocyanate complex as an impurity. Further purification was found to be obtainable with fractional crystalization.

EXAMPLE 2

Toxicity of Ammonium-Silver Complex of Example 1

The ammonium-silver complex solution of Example 1 (33% wt./vol. $AgNO_3$-equivalent concentration) was found to have an LD-50 in rats of about 1.4 ml per kg of body weight. Extrapolating to humans and assuming a human body weight of 70 kg., a lethal dose is estimated to be in excess of one ounce (28 g) and perhaps as much as one pint of solution.

EXAMPLE 3

Dental Testing in Primates

The three monkeys used in this test program are briefly described as follows:
Monkey No. 1: Female, weight 4.8 kg.
Monkey No. 2: Female, weight 6.3 kg.
Monkey No. 3: Female, weight 7.1 kg.

The teeth of monkey No. 1 were microscopically examined 3 days after treatment; for monkey No. 2 this time interval was 20 days; for monkey No. 3 the interval was 62 days. Upper right (UR) teeth were excavated and used as a negative control, i.e., for testing the response to the intermediate inert filling material (a temporary cement referred to as IRM). Lower right (LR) teeth were excavated, treated with Howe's Solution, and filled with IRM. Upper Left (UL) teeth were excavated, treated with the ammonium-silver complex solution of Examples 1 and 2 (selected for its low LD values) and filled with IRM. Excavations in the dentin were made to less than 1.0 mm from the pulp for most specimens, although three LR specimens had from 1.11 to 1.18 mm of remaining dentin above the pulp, one UL specimen had exactly 1.00 mm of remaining dentin, and one UL specimen had 1.08 mm remaining dentin. Teeth were examined for cellular displacement, superficial response, deep response, amount of reparative dentin abscess formation, hemorrhage, and necrosis.

| Product | K-Ag Complex | Na-Ag Complex | $NH_4$-Ag Complex 2nd Crop | $NH_4$-Ag Complex 1st Crop |
|---|---|---|---|---|
| Silver Thiocyanate % | 39.14 | 56.78 | 60.42 | 2.38 |
| Water Soluble Thiocyanate % | 12.87 | 20.39 | 29.73 | 2.18 |
| Nitrate % | 21.60 | 0.47 | 0.38 | 39.77 |
| Sodium % | — | 8.85 | — | — |
| Potassium % | 23.99 | — | — | — |
| Ammonia % | — | — | 9.28 | 20.22 |

Calculations made on the basis of the above analytical data allow the following conclusions: K-Ag complex has a molar ratio AgSCN:KSCN of 1:1 and contains a large amount of the potassium nitrate byproduct. The Na-Ag complex is relatively pure and consists essentially of the 1:1 complex with a small amount of sodium nitrate as an impurity. The second crop of $NH_4$-Ag complex is a relatively pure complex in the molar ratio of $AgSCN:NH_4SCN$ of 1:1.4. This ratio indicates that Filling Material (IRM) Only (Negative Control Category)

The response to cavity preparation and the insertion of the IRM filling was quite minimal. At the three day interval (Monkey No. 1) only one acceptable specimen revealed any response at all, UR-7 with a ½ degree of cellular displacement.

At the 20 day interval (Monkey No. 2) again only one acceptable specimen revealed some cellular displacement (UR-5) but no inflammatory cellular response. Two specimans revealed minimal reparative dentin formation. Hemorrhage occurred in five specimens but appeared to be due to the trauma of resecting the jaws since it appears fresh and lacks pigment-laden macrophages. Hemorrhage was conspicious in all the quadrants of Monkey No. 2.

At the 62 day interval (Monkey No. 3) no cellular displacement was seen and only one specimen revealed a superficial and deep mild chronic inflammation response. The abscess formation in UR-2 was due to the almost zero thickness of remaining dentin and was contrary to the general trend. Minimal reparative dentin formation occurred in four specimens and moderate reparative dentin formation occurred in two specimens.

Considering the extreme closeness to the pulp in all specimens, no remaining dentin thickness exceeding 1 millimeter, this was an unusually mild control response.

Howe's Ammoniacal Solution Reduced with Eugenol; Teeth Filled with IRM (Positive Control Category)

The response to this treatment was most severe according to today's toxicity standards. At the 3 day interval (Monkey No. 1), abscess formations and necrosis appeared in four of 7 specimens, all having remaining dentin thicknesses less than 1.0 mm. It seemed that if silver nitrate reached the pulp tissue a severe lesion developed regardless of the thickness of remaining dentin. If silver nitrate did not touch the pulp, no significant reaction occurred.

By 20 days (Monkey No. 2), despite the severity of the lesions at 3 days, only one abscess was found and appeared in the center of a resolving lesion (LR-6). Other than this abscess, an inflammatory response when present was of a chronic type and occurred only two specimens (LR-2 and LR-3). Reparative dentin formation was present in four of seven specimens as compared to two of six specimens at the three day interval. Also the amount of reparative dentin was greater. The increased prevalence and quantity of reparative dentin are indicative of severe initial reactions.

By 62 days (Monkey No. 3) the tremendous healing power of the monkey was manifested. Only one specimen (LR-8) revealed any inflammatory infiltrate. No abscesses were present or necrosis. Massive reparative dentin formation occurred in three of seven specimens two of which presented large cellular inclusions indicative of a rapid, urgent rate of formation.

It appears that a remaining dentin thickness of 0.75 mm or greater would prevent a severe response in the pulp from this method of treatment.

Hemorrhage was truly present and due to the toxicity of the treatment at the 3 day interval. In response to the early hemorrhage pigment-laden macrophages were found in healing lesions after 62 days.

Test Solution of Example 1: Teeth Filled with IRM

Cellular displacement and cellular inflammatory response occurred in five of seven specimens of the 3 day group (Monkey No. 1) but no abscess formations. Acute cells predominated in three of the five specimens. Only one specimen (UL-6) revealed some tissue necrosis.

By 20 days (Monkey No. 2) three of seven specimens showed a mild degree of chronic inflammatory infiltrate. No acute cells predominated. Minimal reparative dentin occurred in five of the seven specimens at this time.

By 62 days (Monkey No. 3) no inflammatory cells were seen and reparative dentin was present in all seven specimens. The quantity of the reparative dentin resembled that of this same time interval of the negative controls rather than the massive quantities produced by the Howe's Solution.

From the foregoing findings, it will be apparent that the effect of the test (Example 1) solution on the pulp and the tooth in general was minimal and transient. With the Howe Solution/eugenol trial, on the other hand, significant evidence of massive damage was found.

What is claimed is:

1. A method for treating mammalian dental tissue comprising the step of applying a bactericidal amount of a complex salt of silver thiocyanate in an orally acceptable form to said tissue.

2. A method according to claim 1 wherein said dental tissue is adjacent to a cavity created by the effects of dental caries.

3. A method according to claim 2 comprising the further step of packing a dental filling material into said cavity.

4. A method according to claim 1 wherein said complex salt is dissolved in a liquid polar medium at a weight/weight concentration greater than about 5%.

5. A method according to claim 4 wherein said liquid polar medium containing the complex salt is impregnated into an absorbent material and the absorbent material is rubbed against the dental tissue.

6. A method according to claim 4 wherein said liquid polar medium is an aqueous medium selected from the group consisting of essentially pure water, and an aqueous solution of an orally acceptable water soluble thiocyanate salt.

7. A method according to claim 1 wherein said complex salt comprises a double or triple salt of silver thiocyanate and at lest one other thiocyanate salt of a metal which forms an orally acceptable mono-, di-, or trivalent cation.

8. A method according to claim 7 wherein said complex salt of silver thiocyanate has the formula:

$$[Ag(SCN)_x]M_y$$

wherein M is an orally acceptable cation,
$x$ is a number ranging from about 2 to about 6, and
$y$ is a number ranging from about 1 to about 5.

9. A method according to claim 7 wherein said silver complex salt is applied in a form selected from the group consisting of a dry powder, a paste-like suspension or dispersion, and a solution in an orally acceptable polar solvent.

10. A method according to claim 9 wherein said polar solvent is water.

11. A method according to claim 7 wherein said complex salt is a triple salt of silver thiocyanate, ammonium thiocyanate, and ammonium thiosulfate.

12. A method of inhibiting the decay action of cariogenic bacteria in a viable tooth containing carious dental tissue, comprising the steps of:
a. mechanically removing the carious dental tissue from the tooth to form a fillable cavity,
b. treating at least the inside of said fillable cavity with a batericidal amount of silver thiocyanate or a complex salt thereof in an orally acceptable form, and c. filling said fillable cavity with a dental filling material.

13. In a method for disinfecting dental tissue for therapeutic purposes, the improvement which comprises: applying a double or triple salt of silver thiocyanate to said dental tissue in an orally acceptable form.

14. An aqueous solution for treating dental tissues consisting essentially of a substantially nitrate-free, orally acceptable, aqueous solution of a recrystallized, redissolved, essentially water-soluble complex salt of the components consisting essentially of silver thiocyanate and an orally acceptable, relatively water soluble salt consisting of thiocyanate anion and at least one orally acceptable mono-, di-, or tri-valent cation, said essentially water-soluble complex salt having been made by a reaction producing a water-soluble nitrate as a byproduct, said aqueous solution containing: 5–50%, on a weight per volume-of-solution basis, of silver salt, expressed as silver nitrate equivalent; 2–6 moles, per gram-atom of silver, of said mono-, di-, or tri-valent cation, and sufficient water to provide the aqueous solution.

15. An aqueous solution according to claim 14 wherein said relatively water-soluble thiocyanate is ammonium thiocyanate, the ratio of ammonium thiocyanate to silver thiocyanate is 1.4:1, and the amount of silver salt is 33% on the same basis.

16. In a method for disinfecting cariogenic or potentially cariogenic sites for therapeutic purposes, the improvement which comprises: applying a complex salt of the components comprising silver thiocyanate and at least one other thiocyanate salt to said cariogenic or potentially cariogenic sites in an orally acceptable form.

* * * * *

UNITED STATES PATENT AND TRADEMARK OFFICE
CERTIFICATE OF CORRECTION

PATENT NO. : 4,012,839
DATED : March 22, 1977
INVENTOR(S) : William H. Hill

It is certified that error appears in the above-identified patent and that said Letters Patent are hereby corrected as shown below:

Column 1, line 9, for "portentially" read --potentially--.
Column 1, line 17, for "amalagm" read --amalgam--.
Column 1, line 57, for "by papers" read --in papers--.
Column 3, line 10, for "slver" read --silver--.
Column 3, line 17, for "precititate" read --precipitate--.
Column 3, line 44, for "mucu-" read --muc- --.
Column 4, line 37, for "hyrosulfite" read --hydrosulfite--.
Column 4, line 44, for "ramaining" read --remaining--.
Column 5, line 59, periods in formula should be raised,
     --$AgSCN \cdot NH_4SCN \cdot 4(NH_4)_2S_2O_3$--.
Column 6, line 9, for "thiocyanates For" read --thiocyanates. For--.
Column 6, lines 24 and 25, for "penetraton" read --penetration--
Column 6, line 35, for "bagins" read --begins--.
Column 7, line 30, for "by reaction" read --by the reaction--.
Column 7, line 44, for "ammoinium" read --ammonium--.
Column 9, line 18, for "preparation" read --preparations--.
Column 10, lines 1 and 2, for "incolved" read --involved--.
Column 12, line 41, for "lest" read --least--.
Column 12, line 52, delete "silver".

Signed and Sealed this sixteenth Day of August 1977

[SEAL]

Attest:

RUTH C. MASON
Attesting Officer

C. MARSHALL DANN
Commissioner of Patents and Trademarks